United States Patent
Schaerfl, Jr. et al.

(10) Patent No.: US 6,291,703 B1
(45) Date of Patent: Sep. 18, 2001

(54) PREPARATION OF SUBSTITUTED HYDROXYHYDROCINNAMATE ESTERS BY CONTINUOUS TRANSESTERIFICATION USING REACTIVE DISTILLATION

(75) Inventors: Robert Anthony Schaerfl, Jr.; Michael James Day; Sean Peter Piecuch; Ronald Robert Tellier, all of Mobile, AL (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/238,566

(22) Filed: Jan. 28, 1999

Related U.S. Application Data

(60) Provisional application No. 60/074,148, filed on Feb. 9, 1998.

(51) Int. Cl.$^7$ .................................................. C07C 69/76
(52) U.S. Cl. ............................................... 560/75; 560/67
(58) Field of Search ................................. 560/75, 55, 64, 560/67; 422/187, 211, 312; 202/158; 203/DIG. 6

(56) References Cited

U.S. PATENT DOCUMENTS

| | | | |
|---|---|---|---|
| 4,594,444 | 6/1986 | Orban | 560/67 |
| 5,144,058 | * 9/1992 | Nishimura | 560/67 |
| 5,206,414 | 4/1993 | Evans et al. | 560/75 |
| 5,426,206 | 6/1995 | Jung et al. | 556/436 |
| 5,518,699 | * 5/1996 | Kashnitz et al. | 422/211 |
| 5,523,214 | 6/1996 | Horn | 435/52 |
| 5,536,856 | 7/1996 | Harrison et al. | 554/164 |
| 5,563,291 | * 10/1996 | Kleiner | 560/67 |

FOREIGN PATENT DOCUMENTS

| | | |
|---|---|---|
| 57136548 | 8/1982 | (JP) . |
| 2180851 | 7/1990 | (JP) . |
| 2180852 | 7/1990 | (JP) . |

OTHER PUBLICATIONS

Ullmann's Encyclopedia of Industrial Chemistry, 5$^{th}$ Edition, vol. B4, Verlagsgesellschaft, Weinheim, Germany, 1992, pp 88–89, 93–94, 171–172.

* cited by examiner

Primary Examiner—Michael L. Shippen
(74) Attorney, Agent, or Firm—Luther A. R. Hall; Michele A. Kovaleski

(57) ABSTRACT

Substituted hydroxyhydrocinnamate esters of the formula (I)

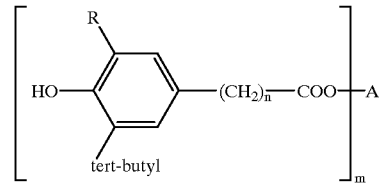

where R is alkyl, n is 0 to 2, m is 1 to 4 and A is alkyl, interrupted or uninterrupted alkylene, alkanetriyl or pentaerythrityl, are prepared by continuous transesterification of the corresponding lower alkyl mono-ester with an alkanol or polyol of the formula A-(OH)$_m$. This novel process comprises continuously introducing into and reacting the reactants in a heated distillation column reactor having a reaction zone which contains a solid, heterogeneous transesterification catalyst to form the compound of formula (I) and the corresponding lower alkanol; separating the products so formed based on their difference in volatility; and continuously removing said products from the distillation column at a steady rate, thereby preventing the reaction mixture from reaching chemical equilibrium. The continuous reaction results in improved product throughput and product quality and has a lower residence time, as compared to known batch-type processes.

31 Claims, 2 Drawing Sheets

Side view:
Corrugated mesh sheet
45° angle

PREPARATION OF SUBSTITUTED HYDROXYHYDROCINNAMATE ESTERS BY CONTINUOUS TRANSESTERIFICATION USING REACTIVE DISTILLATION

This application claims the benefit under 35 USC 119(e) of U.S. Provisional Application No. 60/074,148, filed Feb. 9, 1998.

This invention pertains to a novel process for making substituted higher aliphatic esters of hydrohydroxycinna ic acids by transesterification of the corresponding lower alkyl ester and higher alkanol using a continuous distillation column reactor having a reaction zone containing a solid, heterogeneous transestenification catalyst.

BACKGROUND OF THE INVENTION

The aliphatic esters and polyesters of substituted sterically hindered hydroxyhydrocinnamic acid are well-known as effective antioxidants for a wide variety of organic materials, protecting them from oxidative and thermal degradation. Many of these esters have gained wide spread commercial acceptance as phenolic antioxidants.

Batchwise transesterification methods for obtaining the instant ester compounds are known in the art. For example, methods of obtaining the octadecyl ester of dialkyl hydroxyphenylpropionic acid by ester exchange reaction of the methyl ester of dialkyl hydroxyphenylpropionic acid with octadecyl alcohol in the presence of an alkaline catalyst and the like, are known methods for obtaining higher alkyl esters of 3,5-dialkyl-4-hydroxyphenylpropionic acid by ester exchange reaction between alkyl esters of 3,5-dialkyl-4-hydroxyphenylpropionic acid and alkanols having higher alkyl groups. See, for example, U.S. Pat. Nos. 4,594,444 and 5,206,414. Japanese 57-136,548A teaches an analogous process, but utilizing aromatic sulfonic acids and cationic exchange resins as suitable transesterification catalysts. As noted hereinabove, these known methods involve batchwise-type chemistry, and are therefore readily distinguished from the instant continuous transesterification process for the production of substituted higher aliphatic esters of hydrohydroxycinnamic acids.

Japanese 02-180,851 and 02-180,852 teach a process for the production of B-(3,5-dialkyl-4-hydroxy-5-methylphenyl) propionate by reaction of 2,6-dialkyiphenol with an alkyl acrylate whereby the latter is continuously supplied in an amount of less then 1.0 mole per mole of 2,6-dialkylphenol in the presence of an alkali or alkaline earth 2,6-dialkylphenoxide as catalyst. No mention is made, however, for the continuous removal of the reaction products or of steady-state operation wherein reaction conditions are constant over time.

Reactive distillation methods are known in the art. For example, U.S. Pat. No. 5,536,856 relates specifically to the esterificafion of a carboxylic acid to form the carboxylic acid ester using a reactive column reactor having thereon an ion exchange resin containing sulfonic and/or carboxylic acid groups. U.S. Pat. No. 5,426,206 teaches the use of reactive distillation for the transesterification of a dialkyl carbonate with an aromatic hydroxy compound, such as phenol, in three successive reaction zones, each containing a catalyst such as a titanate ester, to form a diarylcarbonate. Also, the use of reactive distillation for hydrogenation of alkyl fatty acid esters to make the corresponding alkanol is known. However, there is no such method nor analogous method known by which to make the instant hindered phenolic ester compounds.

Indeed, one skilled in the art of antioxidants would not expect continuous transesterification by way of reactive distillation to lead successfully to the instant specialty chemical stabilizer compounds, where ultimate product stability is compromised if antioxidant quality is not high. "Batchwise" methods for preparing the instant compounds, which easily allow for stop-and-start sampling check points, have been historically preferred by industry. Batchwise operation conveniently provides for delays until analytical results become available, and thus allows for consistent and dependable product quality. In contrast, continuous reactive distillation is most often associated with commodity chemicals having lower product specification requirements. The most prevalent example is the manufacture of low molecular weight ethers, which are used as gasoline additives, where high product purity is not a stringent necessity.

BRIEF SUMMARY OF THE INVENTION

Surprisingly, it has now been found that the instant continuous transesterification process using a reactive distillation column reactor results in high product throughout and product quality of substituted higher aliphatic esters of hydroxyhydrocinnamic acids in the ester exchange reaction between the corresponding lower alkyl ester and the higher alkanol. As will become evident from the more detailed description below, the instant process departs from typical reactive distillation techniques in several important aspects, namely by requiring a low pressure difference across the distillation column, by requiring a higher energy input due to the endothermic nature of the system, by requiring a special packing for housing the solid, heterogeneous catalyst, and by requiring a catalyst of a special type.

As compared to known batchwise processes for preparing the instant compounds, the insant continuous transesterification process has several important advantages. Notably, it eliminates the presence of any residual metal catalyst, which interferes with ultimate product stability; reduces unwanted waster and/or byproducts; significantly reduces residence time; and provides consistent product quality since batch-to-batch variation is virtually eliminated.

BRIEF DESCRIPTION OF THE DRAWINGS

Details of the invention and its preferred embodiments will be understood upon reference to the FIGS. 1 and 2, which are diagrangnatic representations of an embodiment of the process of the invention.

DETAILED DESCRIPTION OF THE INVENTION

Figure 1:
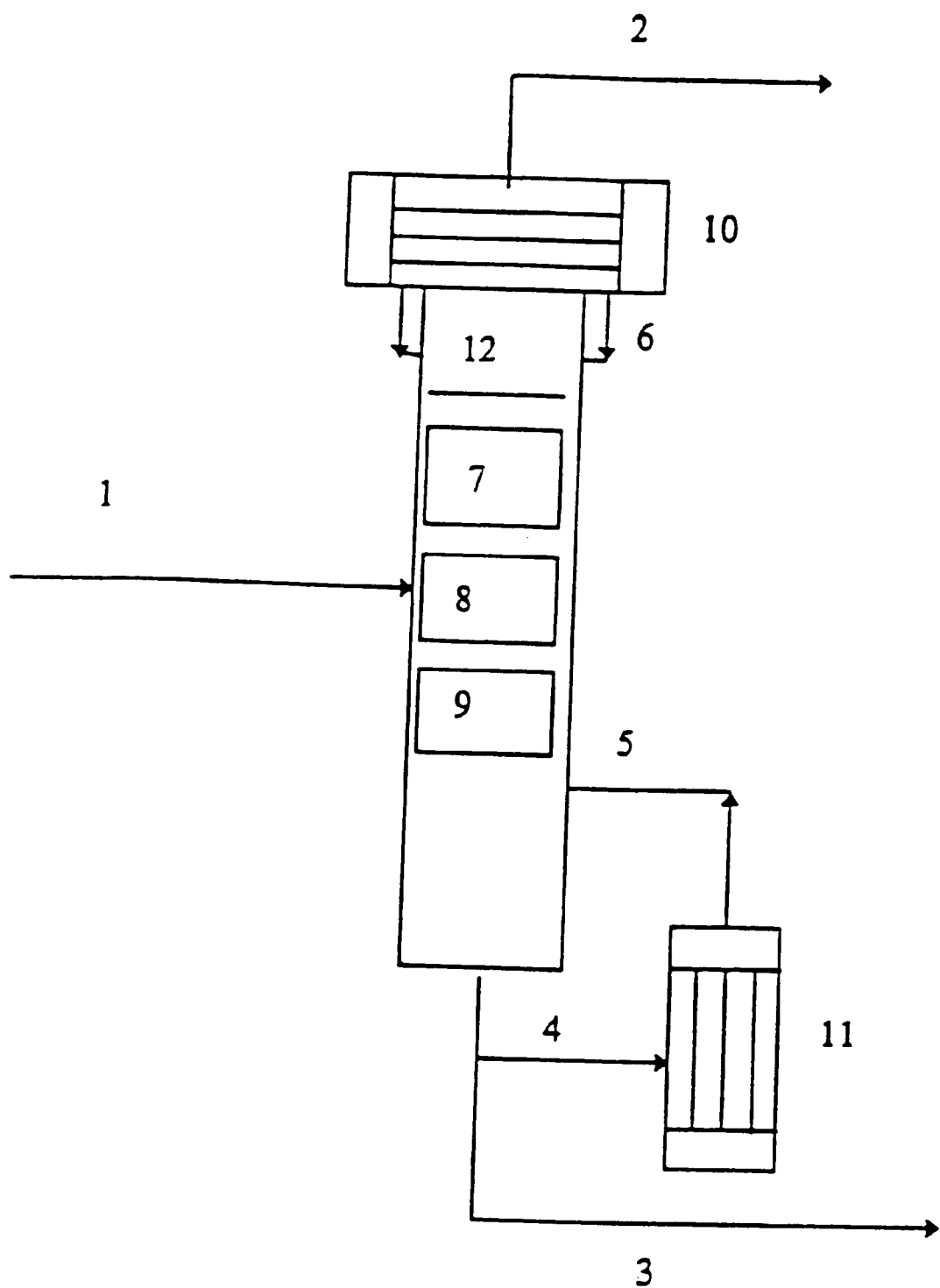

The instant invention pertains to a continuous transesterification process for the preparation of a compound of formula (I)

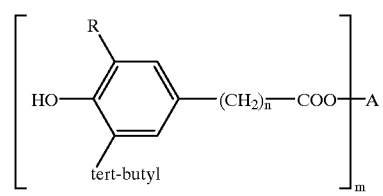

wherein R is an alkyl of 1 to 4 carbon atoms, n is 0 to 2, and m is 1 to 4;

when m is 1, A is a straight or branched chain alkyl of 4 to 18 carbon atoms;

when m is 2, A is a straight or branched chain alkylene of 2 to 12 carbon atoms, or said alkylene interrupted by one to five O or S atoms, or A is 2,2-bis(4-ethyleneoxyphenyl) propane;

when m is 3, A is a straight or branched chain alkanetriyl of 3 to 6 carbon atoms; and when m is 4, A is pentaerythrityl, by reaction of the corresponding lower allyl mono-ester with an alkanol or polyol of the formula A-(OH)$_m$. wherein the process comprises (a) continuously introducing the alkanol or polyol of formula A-(OH)$_m$ and the lower alkyl mono-ester corresponding to formula (I) into a heated distillation column reactor having a reaction zone which contains a solid, heterogeneous transesterification catalyst;

(b) reacting the alkanol or polyol of formula A-(OH)$_m$ and the lower alkyl mono-ester corresponding to formula (I) together in the presence of the transesterification catalyst to form the compound of formula (I) and the corresponding lower alkanol;

(c) separating the less volatile compound of formula (I) from the more volatile lower alkanol by distillation; and (d) removing the compound of formula (I) and the lower alkanol from the distillation column at a steady rate, wherein steps (a)–(d) occur continuously and simultaneously to one another such that the transesterification reaction proceeds at a steady state of operation, thereby preventing the reaction mixture from reaching chemical equilibrium.

Preferably, the lower alkyl ester is a compound of formula (I) where m is 1 and A is methyl or ethyl, most preferably methyl.

Preferably, R is methyl or tert-butyl.

When m is 1, A is preferably alkyl of 8 to 18 carbon atoms; most preferably isooctyl, lauryl or n-octadecyl; especially n-octadecyl.

When m is 2, A is preferably hexamethylene, —CH$_2$CH$_2$SCH$_2$CH$_2$— or —CH$_2$CH$_2$OCH$_2$CH$_2$OCH$_2$CH$_2$—.

When m is 3, A is preferably CH$_3$C(CH$_2$—)$_3$, CH$_3$CH$_2$C(CH$_2$—)$_3$ or glyceryl.

Useful solid, heterogeneous transesterification catalysts can be neutral, slightly acidic or slightly basic. Their acidity or basicity should not be so high as to cause cleavage of the tert-butyl group of the hindered phenolic group at the elevated reaction temperature. The catalyst should be chosen on the basis that it not significantly leach into the reaction mass, although some breakdown and fines are tolerable and may be removed by filtration. Further, the catalyst should be in an appropriate form, i.e., have a diameter of ⅛ inch or smaller to ensure an easy fit into the structured channels of the column reactor. They can be in pellet, spheroid, extrudate or chunk form to allow for and should have the strength to withstand dusting or breakage due to handling or usage in chemical processing. The most preferable product form maximizes surface area while allowing efficient transport of the reaction mass to and from the structured housing unit.

The neutral, slightly basic or slightly acidic solid, heterogeneous transesterification catalysts include, but are not limited to, silicates of Group IVB elements (hafinum, zirconium, titanium and unnilquadium) as the active component, wherein zirconium and titanium are preferred, with the latter being the most preferred. The silicates can be either crystalline, amorphous or a combination thereof. They are generally based on homogeneous mixed oxides of silicon and the said group IVB element. Such catalysts are described in European Patent No. 623,581-A2, incorporated herein by reference.

The transesterification conditions used in step (b) will to a large extent depend upon the activity of the transesterification catalyst. Although the use of elevated pressures is not ruled out, it will normally be preferred to carry out the transesterification reaction below atmospheric pressure, for example, in the range of from about 1 mm Hg to about 400 mm Hg, preferably from about 1 mm Hg to about 100 mm Hg, even more preferably from about 10 mm Hg to about 20 mm Hg. In this way, the vaporization of the lower alkanol formed in step (b) is facilitated during the course of the transesterification reaction. Removal of the lower alkanol during transesterification drives the transesterification reaction towards completion.

When a silicate of a Group IVB element (described hereinabove) is used as the transesterification catalyst, a reaction temperature of between about 100° C. and about 225° C. is typically used. Preferably, the temperature is between about 175° C. and about 215° C.

The reactants are typically employed in a mole ratio wherein the reacting groups (i.e., ester to hydroxy groups) are nearly stoichiometric, that is from about 1.2:0.8 to about 0.8:1.2. Any excess reactant is continuously removed and may be recycled in equipment which is downstream from the reactor.

The transesterification reaction may take place in the presence of an organic solvent, particularly when solvent is needed to dissolve reactant solids which are not rendered molten or when any material is exceptionally viscous or otherwise hard to handle. It may also be beneficial to employ a solvent to improve the wetting of the surface of the packing. The solvent should not have a volatility greater than that of methanol. Representative solvents include, but are not limited to, aromatic hydrocarbons such as benzene, toluene, xylene or the like; aromatic alkoxides such as dimethoxybenzene or the like; aliphatic hydrocarbons such as hexane, heptane or the like; halogenated hydrocarbons; alcohols such as butanol and the like; esters such as ethyl acetate and the like; ketones such as methyl ethyl ketone and the like; solvents such as dimethylformamide, N-methylpyrrolidone and the like, with the preferred solvents not reacting significantly with the reactants. The solvent may be removed from the reaction crude by ordinary means known in the art, for example by fractionation, stripping, thin-film evaporation, wiped-film evaporation, pervaporation and other volatility-based separations, phase separation, liquid-liquid extraction, adsorption, melt crystallization, membrane filtration, chelation, and in particular by flash distillation. In general, if conditions allow, it is preferable to run the transesterification reaction neat in the absence of solvent.

The product stream may be further processed to remove non-product components. Purification may be accomplished by wiped film evaporation, thin-film evaporation, or other volatility-based separations, in order to form a melt product. Alternatively, non-product components may be removed by crystallization, centrifiugation or drying, in order to form a powder product. Additionally, filters such as bag filters, filter presses, cartridge filters and the like may be employed to remove particulates or precipitates from the product.

As already mentioned, steps (a)–(d) of the process according to the invention are preferably conducted simultaneously such that the reaction mass enters and remains in a steady state operation. That is, the reaction enters and remains in a steady state when the temperatures, pressures concentrations and flow rates are all within 5% of a constant value over time such that no buildup or depletion of material takes place inside the process.

In order that the invention may be clearly understood and readily carried into effect, a preferred process for carrying out the invention is described in detail in the accompanying drawing FIG. 1, which is a flow diagram of the instant continuous transesterification process.

It will be understood by those skilled in the art that the drawing is diagrammatic and that further items of equipment such as reflux drums, pumps, vacuum pumps, temperature sensors, pressure sensors, pressure relief valves, control valves, flow controllers, level controllers, holding tanks, storage tanks, and the like, may additionally be required in a commercial plant. The provision of such ancillary items of equipment is in accordance with conventional chemical engineering practice.

The FIG. 1 is representative of a flow of operation of a reactive distillation column for the continuous manufacture of the substituted higher aliphatic esters of hydroxyhydrocinnamates according to the invention. Feed line 1 is fed continuously with the lower alkyl monoester reactant and the higher alkanol or polyol of the formula A-(OH)$_m$. Feed line 1 may also contain small amounts of the higher alkyl ester product if continuous recycling equipment (not shown here) is present downstream in the operation. The feed line 1 is at or near its bubble or boiling point temperature, given the pressure in the column at the feed line's point of entry. Since the pressure is likely to be from about 1 to about 400 mm Hg, the bubble point temperature is thus likely to be from about 100 to about 225° C. Preferably the pressure is from about 10 to about 20 mm Hg and the temperature from about 175 to about 215° C.

The feed of reactants enters the reactive distillation column and comes into contact with packed sections 7, 8 and 9. Upon contact therewith, the feed distills. The feed rate is controlled and held constant by a control valve (not shown). The top packed section 7 (optional) and the bottom packed section 9 (also optional) contain no catalyst and are not reactive. These unreactive packed sections preferably contain a structured packing, most preferably FLEXIPAC® structured packing available from KOCH Engineering Company, Inc., headquartered in Wichita, Kans.

Figure 2:
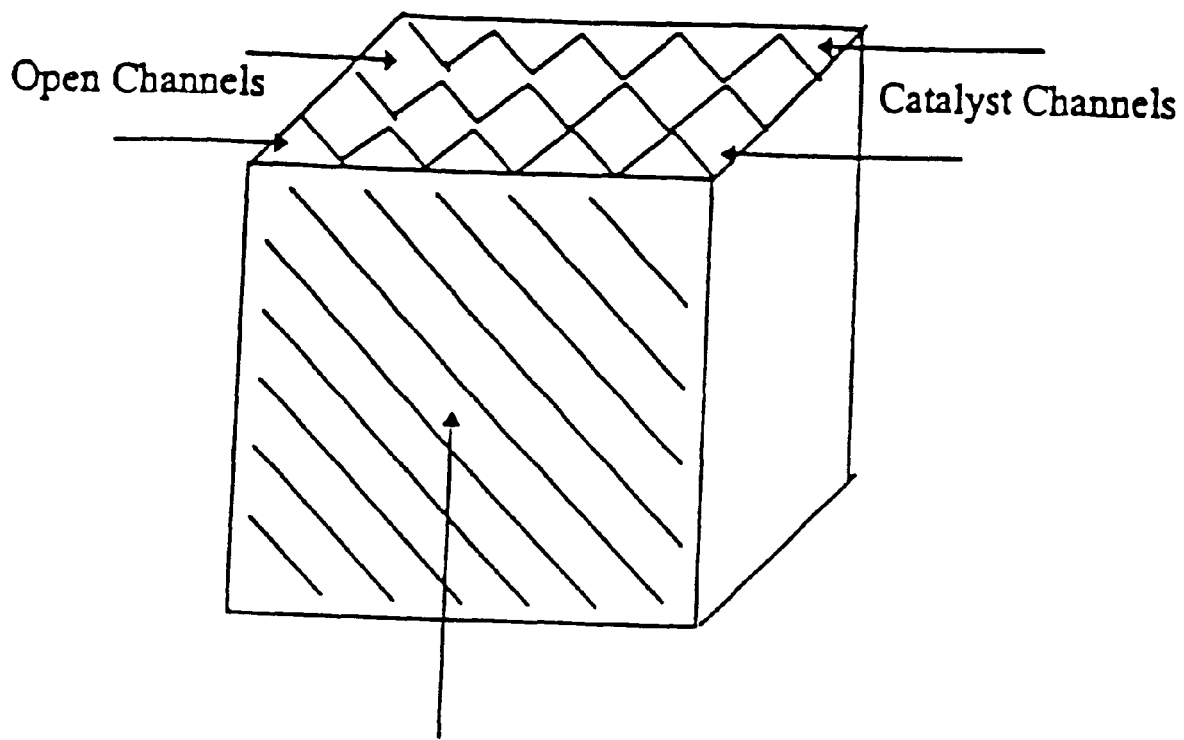

The packed section 8 houses the catalyst and is the reactive portion of the column. FIG. 2, below, describes the packed section 8 in detail. The packed section 8 contains an effective amount of the transesterification catalyst, which is preferably in the form of KATAMAX® structured packing, available from KOCH Engineering Company, Inc. KATAMAX® packing is particularly suitable in the present high temperature and low pressure system.

Alternatively, the packed section 8 may be comprised of a mixture of transesterification catalyst and a random packing material such as PROPAKE®, available from Cannon Instrument Company (State College, Pennsylvania). A mixture of catalyst and packing material is particularly suitable for reactions where a pressure differential across the distillation column is not needed.

It is preferred to utilize packed section 7 which serves to reduce the amount of reactants which may enter the distillate stream 2. This upper section operates at pressures typically from about 1 to about 400 mm Hg, in particular from about 5 to about 10 mm Hg, and at temperatures up to about 200° C., in particular from about 1250 to about 175° C.

It is also preferred to utilize packed section 9 which serves to protect the hydroxyhydrocinnamate ester product from prolonged exposure to the catalyst at high temperature, which conditions have been known to cause cleavage of the butyl group from the hindered phenol moiety. This bottom packed section 9 typically operates at a pressure from about 5 to about 760 mm Hg, preferably 15 to about 30 mm Hg, and at a temperature of from about 150° to about 250° C., preferably about 195° to about 240° C.

The liquid exiting the reactive distillation column is the bottoms stream and is divided into a crude stream 3 and a reboil stream 4. The crude stream 3 continues to downstream processing equipment where the final product is isolated. The reboil stream 4 is pumped through a reboiler which heats and vaporizes a fraction of the reboil stream, called the reboiler stream 5. Reboiler stream 5 is the primary means of adding heat to the reactive distillation column and should be at a temperature high enough for effective distillation of the lower alkanol product, but low enough so as not to cause cleavage of the butyl group of the hindered phenol group of the product of formula (I). In general, the temperature should typically be on the order of about 100° to about 250° C., preferably about 240° C. The liquid exiting the reboiler goes to the bottom of the column. From there, the stream exits through the bottom and then splits, with a portion recycled back through the reboiler and a portion moving downstream to product isolation equipment.

The vapor containing the lower alkanol product and other components is distilled through the reactive distillation column to the condenser 10, which serves to remove heat from the column and return a fraction of the vapor to the liquid state. The liquid fraction 6 consists chiefly of components which are free of the lower alkanol product. The vapor fraction or distillate stream 2 containing the lower alkanol product continues to waste disposal equipment (not shown) or to a downstream process unit (not shown) to recover residual feedstock.

The liquid fraction 6 continues to a distributor 12 to spread the liquid over the top packed section 7 or 8. Its temperature is generally on the order of about 100° to about 175° C. and depends on the reflux ratio, that is, on how large the liquid fraction 6 is compared to the distillate stream 2.

The FIG. 2 represents a side view of the KATAMAX® structured packing, mentioned hereinabove. A section of packing consists of a plurality of corrugated mesh sheets 1 with diagonal ridges. The sheets are placed side by side in such a manner as to alternate them so that the ridges are perpendicular to one another. Each set of two sheets is welded together to form an envelope. Every other row of envelope holds the solid transesterification catalyst in catalyst channels 2, with the alternating row forming an open channel 3, which remains empty.

The distillation column further comprises a side draw; a pumparound loop; or a plurality of reaction zones containing a solid, heterogeneous transesterification catalyst which is the same or different. Two or more distillation columns can be connected in series where each column, independently of the other, has a solid, heterogeneous transesterification catalyst.

The following examples are not to be construed to limit the scope of the instant invention in any manner whatsoever.

EXAMPLE 1

Octadecyl 3,5-Di-tert-butyl-4-hydroxyhydrocinnamate

The reactants, 99.9 g (0.369 mole) of octadecyl alcohol and 105.0 g (0.359 mole) of methyl 3,5-di-tert-butyl-4-hydroxyhydrocinnamate are melted and poured into a roundbottom glass flask containing a magnetic stir bar. The flask is fitted with a silvered-glass column to the top of which is connected a knockback condenser. A mixture of 4.5 ounces each of PROPAK® random packing (67.7 g) and TiS catalyst (125.0 g) are placed in the column and supported by an inverted conical screen. A heating bath is employed to supply hot oil to the condenser at a temperature above 120° C.

The mixture in the flask is brought to reflux at a pressure of 3 mm Hg and a temperature of between 184 and 227° C. As the reactants enter the reaction zone containing the PROPAK®/TiS mixture, they react to form the title compound and methanol, and distill simultaneously. The vapors (consisting of the reactants and the title compound) leave the reaction zone and come into contact with the knockback condenser. The methanol passes through the condenser and is recovered using a vacuum trap. The reactants are knocked back to the reaction flask. The liquid exiting the bottom of the reaction zone consists of the reactants and the title compound. After four hours, analysis of the contents of the reaction flask using Gas Chromatography shows a mixture of 84.8 wt % of the title compound, 4.7 wt % of methyl 3,5-di-tert-butyl-4-hydroxyhydrocinnamate and 5.5 wt % octadecyl alcohol.

EXAMPLE 2

Octadecyl 3,5-Di-tert-butyl-4-hydroxyhydrocinnamate

The general procedure of Example 1 is repeated with appropriately modified equipment, using KATAMAX® packing containing TiS catalyst. The title compound is obtained in yield and purity similar to that of Example 1.

EXAMPLE 3

Octadecyl 3,5-Di-tert-butyl-4-hydroxyhydrocinnamate

The general procedure of Example 1 is repeated, but using 337.0 g (1.246 mole) of octadecyl alcohol and 391.9 g (1.340 mole) of methyl 3,5-di-tert-butyl-4-hydroxyhydrocinnamate and a reflux temperature of between 189 and 201° C. After 2.5 hours, analysis of the contents of the reaction flask using Gas shows a mixture of 32.1 wt % of the title compound, 32.0 wt % of methyl 3,5-di-tert-butyl-4-hydroxyhydrocinnamate and 29.6 wt % octadecyl alcohol.

EXAMPLE 4

Octadecyl 3,5-Di-tert-butyl-4-hydroxyhydrocinnamate

The general procedure of Example 3 is repeated with appropriately modified equipment, using KATAMAX® packing containing TiS catalyst. The title compound is obtained in yield and purity similar to that of Example 3.

EXAMPLE 5

Octadecyl 3,5-Di-tert-butyl-4-hydroxyhydrocinnamate

The general procedure of Example 1 is repeated, but using 382.9 g (1.416 mole) of octadecyl alcohol and 471.3 g (1.612 mole) of methyl 3,5-di-tert-butyl-4-hydroxyhydrocinnamate and employing 2 ounces (30.1 g) of PROPAK® and 2.5 ounces (69.4 g) of TiS catalyst. The system is brought to reflux at a pressure of 6–8 mm Hg and a temperature of between 190 and 202° C. After 2.5 hours, analysis of the contents of the reaction flask using Gas Chromatography shows a mixture of 51.7 wt % of the title compound, 26.2 wt % of methyl 3,5-di-tert-butyl-4-hydroxyhydrocinnamate and 20.8 wt % octadecyl alcohol.

EXAMPLE 6

Octadecyl 3,5-Di-tert-butyl-4-hydroxyhydrocinnamnate

The general procedure of Example 5 is repeated with appropriately modified equipment, using KATAMAX® packing containing TiS catalyst. The title compound is obtained in yield and purity similar to that of Example 5.

EXAMPLES 7–10

Using the general procedure of any of Examples 1–6 with either a methyl or ethyl ester of a substituted hydroxyhydrocinnamic acid and various alkanols, the following higher esters of formula (I) are obtained in high yield and purity.

| Example | R | A |
|---|---|---|
| 7 | tert-butyl | lauryl |
| 8 | tert-butyl | n-octadecyl |
| 9 | tert-butyl | n-octyl |
| 10 | tert-butyl | isooctyl |

EXAMPLES 11–18

Using the general procedure of any of Examples 1–6 with either the methyl or ethyl ester of a substituted hydroxyhydrocinnamic acid and various polyols, the following higher esters of formula (I) are obtained in high yield and purity.

| Example | n | R | A |
|---|---|---|---|
| 11 | 2 | tert-butyl | hexamethylene |
| 12 | 2 | methyl | —CH$_2$CH$_2$SCH$_2$CH$_2$— |
| 13 | 2 | tert-butyl | —CH$_2$CH$_2$SCH$_2$CH$_2$— |
| 14 | 2 | tert-butyl | —CH$_2$CH$_2$(OCH$_2$CH$_2$)$_2$— |
| 15 | 3 | tert-butyl | CH$_3$C(CH$_2$-)$_3$ |
| 16 | 3 | tert-butyl | CH$_3$C(CH$_2$-)$_3$ |
| 17 | 4 | tert-butyl | pentaerythrityl |
| 18 | 4 | methyl | pentaerythrityl |

What is claimed is:

1. A continuous transesterification process for the preparation of a compound of formula I

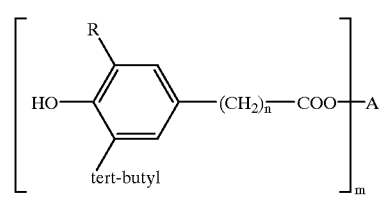

wherein
R is alkyl of 1 to 4 carbon atoms;
n is 0, 1 or 2;
m is 1, 2, 3 or 4;

when m is 1, A is a straight or branched chain alkyl of 4 to 18 carbon atoms;

when m is 2, A is a straight or branched chain alkylene of 2 to 12 carbon atoms, or said alkylene interrupted by one to five O or S atoms, or A is 2,2-bis(4-ethyleneoxyphenyl)propane;

when m is 3, A is a straight or branched chain alkanetriyl of 3 to 6 carbon atoms; and when m is 4, A is pentaerythrityl;

by reaction of the corresponding lower alkyl mono-ester with an alkanol or polyol of formula A-$(OH)_m$ wherein the process comprises (a) continuously introducing the alkanol or polyol of formula A-$(OH)_m$ and the lower alkyl mono-ester corresponding to formula I into a heated distillation column reactor having a reaction zone which contains a solid, heterogeneous transesterification catalyst at a pressure of from about 1 to about 400 mm Hg;

(b) reacting the alkanol or polyol of formula A-$(OH)_m$ and the lower alkyl mono-ester corresponding to formula I together in the presence of the transesterification catalyst to form the compound of formula I and the corresponding lower alkanol;

(c) separating the less volatile compound of formula I from the more volatile alkanol by distillation, and (d) removing the compound of formula I and the lower alkanol from the distillation column at a steady rate, wherein steps (a)–(d) occur continuously and simultaneously to one another such than the transesterification reaction proceeds at a steady state of operation, thereby preventing the reaction mixture from reaching chemical equilibrium.

2. A process according to claim 1 where the lower alkyl ester is methyl or ethyl 3,5-di-tert-butyl-4-hydroxyhydrocinnate.

3. A process according to claim 2 where the lower alkyl ester is methyl 3,5-di-tert-butyl-4-hydroxyhydrocinnamate.

4. A process according to claim 1 where, in the compounds of formula (I), R is methyl or tert-butyl.

5. A process according to claim 1 where, in the compound of formula (I), m is 1, and A is alkyl of 8 to 18 carbon atoms.

6. A process according to claim 5 wherein A is isooctyl, lauryl or n-octadecyl.

7. A process according to claim 6 wherein A is n-octadecyl.

8. A process according to claim 1 where, in the compound of formula (I), m is 2 and A is hexamethylene, $-CH_2CH_2SCH_2CH_2-$ or $-CH_2CH_2OCH_2CH_2OCH_2CH_2-$.

9. A process according to claim 1 where, in the compound of formula (I), m is 3 and A is $CH_3C(CH_2-)_3$, $CH_3CH_2C(CH_2-)_3$ or glyceryl.

10. A process according to claim 1 wherein the compound of formula (I) is isooctyl 3,5-di-tert-butyl-4-hydroxyhydrocinnamate, n-octadecyl 3,5-di-tert-butyl-4-hydroxyhydrocinnamate, or pentaerythrityl tetrakis(3,5-di-tert-butyl-4-hydroxyhydrocinnamate).

11. A process according to claim 1 wherein the solid, heterogeneous transesterification catalyst is a silicate of a Group IVB element.

12. A process according to claim 11 wherein the solid, heterogeneous transesterification catalyst is titanium on silica.

13. A process according to claim 1 where the reactants are introduced into the reactive distillation column such that the reacting groups (i.e., ester to hydroxy groups) are present in a molar ratio of about 1.2:0.8 to about 0.8:1.2.

14. A process according to claim 1 where the transesterification reaction is run neat without the addition of solvent.

15. A process according to claim 1 wherein the alkanol or polyol of formula A-$(OH)_n$ and the lower alkyl ester corresponding to formula (I) are heated to near the bubble point prior to introduction into the distillation column.

16. A process according to claim 1 wherein the reactive distillation column comprises a reactive packed middle section which houses the transesterification catalyst and one or both of an optional nonreactive top and bottom packed section.

17. A process according to claim 16 wherein the column comprises both the top and bottom packed sections.

18. A process according to claim 16 wherein the optional top and bottom packed section(s) is/are in the form of FLEXIPAC® structured packing.

19. A process according to claim 1 wherein the solid, heterogeneous transesterification catalyst is housed in a structured packing.

20. A process according to claim 19 wherein the structured packing is in the form of KATAMAX® structured packing.

21. A process according to claim 1 wherein the solid, heterogeneous transesterification catalyst is mixed with random packing.

22. A process according to claim 21 wherein the random packing is in the form of PROPAK®.

23. A process according to claim 16 wherein the distillation column further comprises a side draw.

24. A process according to claim 16 wherein the distillation column further comprises a pump-around loop.

25. A process according to claim 1 wherein any unreacted alkanol or polyol of formula A-$(OH)_n$ and/or lower alkyl ester corresponding to formula (I) are recovered in downstream apparatus and subsequently recycled.

26. A process according to claim 1 wherein the distillation column is comprised of a plurality of reaction zones containing a solid, heterogeneous transesterification catalyst which is the same or different.

27. A process according to claim 1 wherein two or more distillation columns are connected in series where each column, independently of the other, has a solid, heterogeneous transesterification catalyst.

28. A process according to claim 1 wherein the transesterification reaction takes place at a temperature of between about 100° C. and about 225° C.

29. A process according to claim 28 wherein the temperature is from about 175° C. to about 215° C.

30. A process according to claim 1 wherein the transesterification reaction takes place at a pressure of from about 1 to about 100 mm Hg.

31. A process according to claim 30 wherein the pressure is from about 10 to about 20 mm Hg.

* * * * *